United States Patent [19]
Peck et al.

[11] Patent Number: 5,834,308
[45] Date of Patent: Nov. 10, 1998

[54] IN VITRO GROWTH OF FUNCTIONAL ISLETS OF LANGERHANS

[75] Inventors: Ammon B. Peck; Janet G. Cornelius, both of Gainesville, Fla.

[73] Assignee: University of Florida Research Foundation, Inc., Gainesville, Fla.

[21] Appl. No.: 234,071

[22] Filed: Apr. 28, 1994

[51] Int. Cl.$^6$ .............................. C12N 5/00; C12N 5/02
[52] U.S. Cl. .................. 435/325; 435/354; 435/366; 435/371; 435/41; 435/70.1; 435/70.3
[58] Field of Search .......................... 435/240.1, 240.2, 435/240.21, 240.3, 240.31, 70.1, 70.3, 325, 354, 366, 371, 41

[56] References Cited

FOREIGN PATENT DOCUMENTS

| | | |
|---|---|---|
| 0363125 | 4/1990 | European Pat. Off. . |
| 8601530 | 3/1986 | WIPO . |
| 9300441 | 1/1993 | WIPO . |
| 9423572 | 10/1994 | WIPO . |

OTHER PUBLICATIONS

Takaki, In Vitro Cell Dev. Biol., 25(9):763–69 (1989).
Kuo et al., Clinical Research, 38(1):58A (1990).
Rao et al., Cell Differ. Dev., 29(3):155–63 (1990).
Yu et al., Tianjin Medical Journal, 18(11):643–47 (1990).
Brelji et al., Diabetes, 43(2):263–73 (1994).
Vinik et al., Adv. Exp. Med. Biol., 321, pp. 1–5 (1992).
Teitelman, Tumor Biol, 14(3):167–73 (1993).
Hamashima et al, *Cellular, Molecular & Genetic Approaches to Immunodiagnosis & Immunotherapy*, pp. 219–226 (1987).
Nielsen, ACTA Endocrinologica, Suppl. 266 (1985).
S. Baekkeskov et al. (1990) "Identification of the 64K autoantigen in insulin–dependent diabetes as the GABA–synthesizing enzyme glutamic acid decarboxylase" Nature 347:151–156.
S. Baekkeskov et al. (1982) "Autoantibodies in newly diagnosed diabetic children immunoprecipitate human pancreatic islet cell proteins" Nature 298:167–169.
Bendelac et al. (1987) "Syngenic Transfer of Autoimmune Diabetes from Diabetic NOD Mice to Healthy Neonates" J. Exp. Med. 166:823–832.
A. Bendelac et al. (1988) "Adoptive T Cell Transfer of Autoimmune Nonobese Diabetic Mouse Diabetes Does Not Require Recruitment of Host B Lymphocytes" The Journal of Immunology 141(8):2625–2628.

T. Hanafusa et al. (1988) "Induction of Insulitis by Adoptive Transfer with L3T4+Lyt2–T–Lymphocytes in T–Lymphocyte–Depleted NOD Mice" Diabetes 37:204–208.
A.J. Jarpe et al. (1991) "Flow Cytometric Enumeration of Mononuclear Cell Populations Infiltrating the Islets of Langerhan in Prediabetic NOD Mice: Development of a Model of Autoimmune Insulitis for Type I Diabetes" REgional Immunology 3:305–317.
B.J. Miller et al. (1988) "Both the Lyt–2+ and L3t4+ Cell Subsets are Required for the Transfer of Diabetes in Nonobese Diabetic Mice" The Journal of Immunology 140(1):52–58.
O. Pontesilli et al. (1987) "Circulating lymphocyte populations and antoantibodies in non–obese diabetic (NOD) mice: a longitudinal study" Clin. Exp. Immunol. 70:84–93.
S. Reddy et al. (1988) "Ontogeny of islet cell antibodies, insulin autoantibodies and insulitis in the non–obese diabetic mouse" Diabetologia 31:322–328.
A. Signore et al. (1989) "The natural history of lymphocyte subsets infiltrating the pancreas of NOD mice" Diabetologia 32:282–289.
Y. Wang et al. (1987) "Autoimmune Diabetes in NOD Mouse in L3T4 T–Lymphocyte Dependent" Diabetes 36:535–538.
McEvoy, R.C., P.E. Leung (1982) "Tissue Culture of Fetal Rat Islets: Comparison of Serum–Supplemented and Serum- Free, Defined Medium on the Maintenance, Growth, and Differentiation of A, B, and D Cells" Endocrinology 111(5):1568–1575.
Gazdar, A.F. et al. (1980) "Continuous, clonal, insulin–and somatostatin–secreting cell lines established from a transplantable rat islet cell tumor" Proc. Natl. Acad. Sci. USA 77(6):3519–3523.
Korsgren, O. et al. (1993) "In vitro Screening of Putative Compounds Inducing Fetal Porcine Pancreatic β–cell Differentiation: Implications for Cell Transplantation in Insulin–Dependent Diabetes Mellitus" Upsala Journal of Medical Sciences 98(1):39–50.

*Primary Examiner*—Leon B. Lankford, Jr.
*Attorney, Agent, or Firm*—Swanson & Bratschun, L.L.C.

[57] ABSTRACT

The subject invention concerns new methods which make it possible, for the first time, to grow functional islet cells in in vitro cultures. The ability to grow these cells opens up important new avenues for research and therapy relating to diabetes.

10 Claims, 2 Drawing Sheets

IN VITRO GROWTH OF FUNCTIONAL ISLETS OF LANGERHANS

BACKGROUND OF THE INVENTION

Diabetes is a major public health problem. As presented in the 1987 Report of The National Long-Range Plan to Combat Diabetes commissioned by the National Diabetes Advisory Board, six million persons in the United States are known to have diabetes, and an additional 5 million have the disease which has not yet been diagnosed. Each year, more than 500,000 new cases of diabetes are identified. In 1984, diabetes was directly causal in 35,000 American deaths and was a contributing factor in another 95,000.

Ocular complications of diabetes are the leading cause of new cases of legal blindness in people ages 20 to 74 in the United States. The risk for lower extremity amputation is 15 times greater in individuals with diabetes than in individuals without it. Kidney disease is a frequent and serious complication of diabetes. Approximately 30 percent of all new patients in the United States being treated for end-stage renal disease have diabetes. Individuals with diabetes are also at increased risk for periodontal disease. Periodontal infections advance rapidly and lead not only to loss of teeth but also to compromised metabolic function. Women with diabetes risk serious complications of pregnancy. Current statistics suggest that the mortality rates of infants of mothers with diabetes is approximately 7 percent.

Clearly, the economic burden of diabetes is enormous. Each year, patients with diabetes or its complications spend 24 million patient-days in hospitals. A conservative estimate of total annual costs attributable to diabetes is at least $24 billion (American Diabetes Association est., 1988); however, the full economic impact of this disease is even greater because additional medical expenses often are attributed to the specific complications of diabetes rather than to diabetes itself.

Diabetes is a chronic, complex metabolic disease that results in the inability of the body to properly maintain and use carbohydrates, fats, and proteins. It results from the interaction of various hereditary and environmental factors and is characterized by high blood glucose levels caused by a deficiency in insulin production or an impairment of its utilization. Most cases of diabetes fall into two clinical types: Type I, or juvenile-onset, and Type II, or adult-onset. Type I diabetes is often referred to as Insulin Dependent Diabetes, or IDD. Each type has a different prognosis, treatment, and cause.

Approximately 5 to 10 percent of diabetes patients have IDD. IDD is characterized by a partial or complete inability to produce insulin usually due to destruction of the insulin-producing $\beta$ cells of the pancreatic islets of Langerhans. Patients with IDD would die without daily insulin injections to control their disease.

Few advancements in resolving the pathogenesis of diabetes were made until the mid-1970s when evidence began to accumulate to suggest that IDD had an autoimmune etiopathogenesis. It is now generally accepted that IDD results from a progressive autoimmune response which selectively destroys the insulin-producing $\beta$ cells of the pancreatic islets of Langerhans in individuals who are genetically predisposed. Autoimmunity to the $\beta$ cell in IDD involves both humoral (Baekkeskov et al., 1982; Baekkeskov et al., 1990; Reddy et al. 1988; Pontesilli et al., 1987) and cell-mediated (Reddy et al. 1988; Pontesilli et al., 1987; Wang et al., 1987) immune mechanisms. Humoral immunity is characterized by the appearance of autoantibodies to $\beta$ cell membranes (anti-69 kD and islet-cell surface autoantibodies), $\beta$ cell contents (anti-carboxypeptidase $A_1$, anti-64 kD and/or anti-GAD autoantibody), and/or $\beta$ cell secretory products (anti-insulin). While serum does not transfer IDD, anti-$\beta$ cell autoantibody occurs at a very early age, raising the question of an environmental trigger, possibly involving antigenic mimicry. The presence of cell-mediated immunological reactivity in the natural course of IDD is evidenced by an inflammatory lesion within the pancreatic islets, termed insulitis. Insulitis, in which inflammatory/immune cell infiltrates are clearly visible by histology, has been shown to be comprised of numerous cell types, including T and B lymphocytes, monocytes and natural killer cells (Signore et al., 1989; Jarpe et al. 1991). Adoptive transfer experiments using the NOD (non-obese diabetic) mouse as a model of human IDD have firmly established a primary role for auto-aggressive T lymphocytes in the pathogenesis of IDD (Bendelac, et al., 1987; Miller et al., 1988; Hanafusa et al., 1988; Bendelac et al., 1988). Unfortunately, the mechanisms underlying destruction of the pancreatic $\beta$ cells remain unknown.

Numerous strategies (e.g., bone marrow replacement, immunosuppressive drugs and autoantigen immunizations) have been investigated as possible means to arrest the immunological attack against the pancreatic $\beta$ cells. However, for these approaches to be effective, individuals who will eventually develop clinical disease must be identified. Most often, patients are identified too late for effective intervention therapy since the immunological attack has progressed to a point where a large percentage of the $\beta$ cells have already been destroyed. Because the $\beta$ cell is thought to be an end-stage differentiated cell, it is believed that the body has little capacity to regenerate new $\beta$ cells, thus necessitating regular life-long insulin therapy. Recently, one approach to overcome this problem has been islet cell transplantation. Islet cell transplantation has the disadvantage that the islets are allogeneic which, in turn, can invoke an allo-immune response. Thus, there would be major advantages to growing islets of Langerhans containing functional $\beta$ cells directly from IDD patients.

BRIEF SUMMARY OF THE INVENTION

The subject invention concerns the discovery that functional islets containing insulin-producing $\beta$ cells can be grown in long-term cultures from single pluripotent stem cells.

The unique procedure of the subject invention takes advantage of the discovery that pluripotent stem cells exist in the pancreas of even adult individuals. The cells can be cultured in a high amino acid medium supplemented with normal serum which is derived from the same mammalian species which serves as the origin of the islet cells (homologous serum). This culture is then left undisturbed for several weeks to permit establishment of stromal cells. Once this layer is mature, cell differentiation can be initiated by adding normal serum. After an additional period of growth, functional islets containing cells which produce insulin can then be recovered using standard techniques.

It was not previously known or suspected that pancreatic cells could be used to grow new $\beta$ cells in culture. The fortuitous discovery of culture techniques for growing islets eliminates what had previously been a substantial and long standing barrier to research which will enable a better understanding of the mechanisms of diabetes. Furthermore, the ability to grow islet cells in culture will now make certain therapies for diabetes possible for the first time. For example, in accordance with the subject invention new autologous islets from diabetic individuals can be given to a patient as a way to eliminate the need for insulin therapy because the cultured islet cells are able to produce insulin.

The subject invention also greatly facilitates genetic engineering of β cells to resist subsequent immunological destruction. For example, the cultured islet cells can be transformed to express a protein or peptide which will inhibit or prevent the destructive immune process.

Thus, the ability to grow functioning islets from prediabetic adults represents a major technical breakthrough and facilitates the use of new strategies for treating IDD. The discovery that pluripotent stem cells exist in adult pancreas circumvents the need to use fetal tissue.

DETAILED DESCRIPTION OF THE INVENTION

Figure 1A:
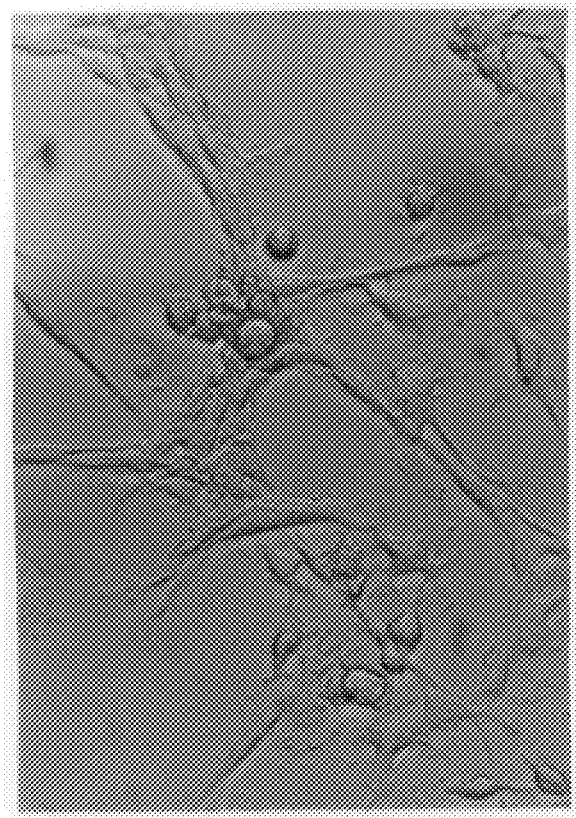
FIGS. 1A through 1D show cells grown according to the procedures of the subject invention.
Figure 1B:
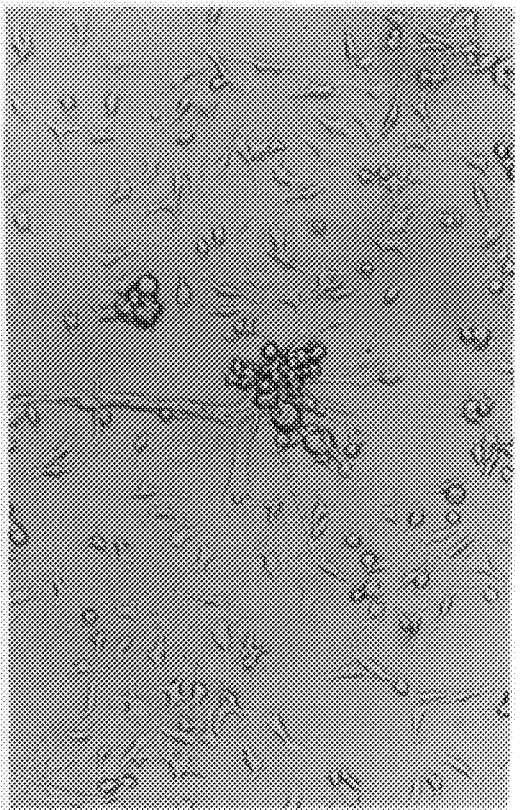
Figure 1C:
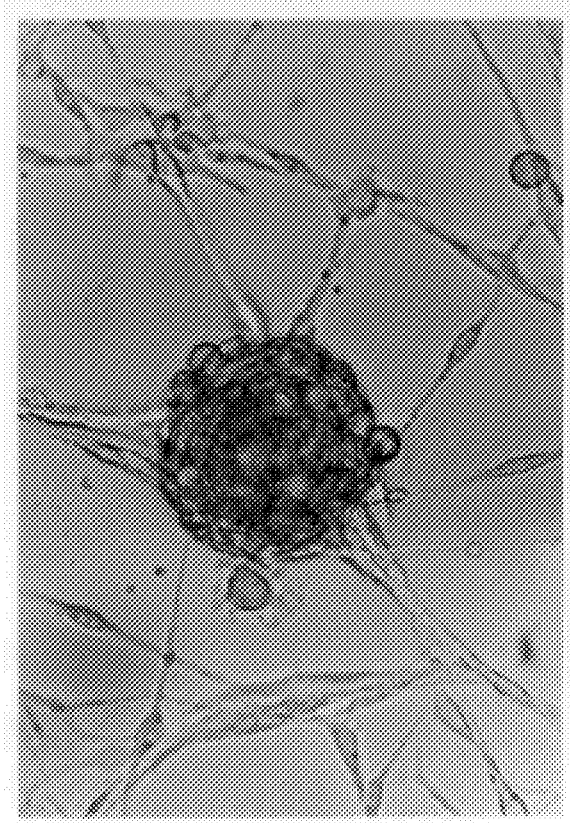

According to the subject invention, functional islets of Langerhans can for the first time be grown in in vitro cultures. The techniques of the subject invention result in cell cultures which produce insulin. The ability to grow these functional cell cultures enables those skilled in the art to carry out procedures which were not previously possible.

The method of the subject invention involves making suspensions of islet cells from the pancreas of a mammal. Preferably, the islet cells would be from the pancreas of a prediabetic mammal. The suspensions are made using standard techniques preferably in a nutrient medium which is high in amino acids. One such medium is known as Click's EHAA medium and is well known and readily available to those skilled in the art. Other equivalent nutrient mediums could be prepared and utilized by those skilled in the art. The medium used to suspend the islet cells is advantageously supplemented by normal serum from the same species of mammal from which the islet cells originate. Thus, in the case of mouse islets the medium is supplemented with normal mouse serum and in the case of human islet cells the medium is supplemented with normal human serum. The preparation of normal serum is well known to those skilled in the art. The concentration of normal serum can range from about 0.5% to about 10% and, for mice is preferably about 1%. For human serum a higher concentration is preferred. This higher concentration may be, for example, about 5%. The cells are then incubated, preferably at about 35°–40° C. and, preferably, in about 5% $CO_2$ atmosphere. This incubation period is, thus, carried out utilizing standard procedures well known to those skilled in the art. The cell culture is then left undisturbed without feeding for several weeks. Preferably, the cultures are not disturbed for at least about 3 weeks. During this time stromal cells proliferate and establish a monolayer which will ultimately give rise to islet cells. The initiation of cellular differentiation can be brought about by refeeding the cultures with Click's EHAA medium supplemented with normal serum as discussed above. Rapid refeeding was found to induce extensive foci of differentiation. The rate of refeeding can be, for example, at one week intervals.

We have been able to propagate and expand islet-producing cultures through serial transfer of islet-derived stromal cells to new culture flasks. This facilitates generating sufficient numbers of islets to reverse the metabolic problems of IDD. It is also now possible to test the capacity of culture-grown islets to reverse hyperglycemia in vivo and to examine and study the immunological response against these newly implanted islets.

In a preferred embodiment of the subject invention the progression of diabetes can be slowed or halted by reimplantation of autologous islets engineered to be resistant to specific factors involved in the immunological attack. For example, the islets can be engineered so that they are resistant to cytotoxic T cell-derived interferon-γ. The availability of long-term cultures of whole islets can also be used in investigations into the pathogenesis of IDD, including the cellular recognition of β cells, the mode of islet infiltration, and the immune mechanisms of β cell destruction. Furthermore, this technology will facilitate islet transplantation, autologous islet replacement, and even development of artificial islets.

The following examples illustrate procedures, including the best mode, for practicing the invention. These examples should not be construed as limiting. All percentages are by weight and all solvent mixture proportions are by volume unless otherwise noted.

EXAMPLE 1

Culturing of Fuction Islets of Longerhan

Single cell suspensions of islet cells were prepared from whole islets isolated from 19–20 week old prediabetic male NOD/UF mice, as detailed elsewhere (Shieh et al., 1993). In our NOD colony, approximately 25% of the male mice will have overt IDD at this age and all will have severe insulitis. The islet cells were resuspended in Click's EHAA medium supplemented with normal mouse serum (NMS) to 1% (Peck et al., 1973), plated in a 25 $cm^2$ tissue culture flask, and incubated at 37° C. in a 5% $CO_2$ atmosphere. At this stage, two outcomes are possible: first, the islet-infiltrating cells may dominate, thus permitting the establishment of immune cell lines, or second, stromal-like cells may dominate, thus allowing the growth of a "nurse cell" monolayer. Growth of stromal-like cell monolayers appeared to result when islet-infiltrating cells were plated simultaneously but in limited numbers. Enrichment of the islet cells with decreased numbers of infiltrating cells can be achieved by gradient separation (Jarpe et al., 1991). Stromal cell cultures, when left undisturbed for 4–5 weeks (i.e., no refeeding) proliferated to cover the entire bottom surface of the culture vessel. From this monolayer of cells, small rounded cells appeared almost as if budding from the stromal cell layer.

Differentiation of the cultures was initiated by refeeding the cultures with Click's EHAA medium supplemented with NMS. Rapid refeeding induced increasing numbers of foci of differentiation. At peak production, as many as 150–200 centers of islet growth occurred simultaneously in a single 25 $cm^2$ T flask. As the cell proliferation and differentiation proceeded, the organization of the islet took place and even appeared to surround itself in a capsular material. The islets generally grew to a constant size (although several grew to about twice the general size), then split off the stromal layers to float in the medium. These free-floating islets tended to break down within 48–72 hours, similar to isolated pancreatic islets cultured under similar conditions.

Figure 2:
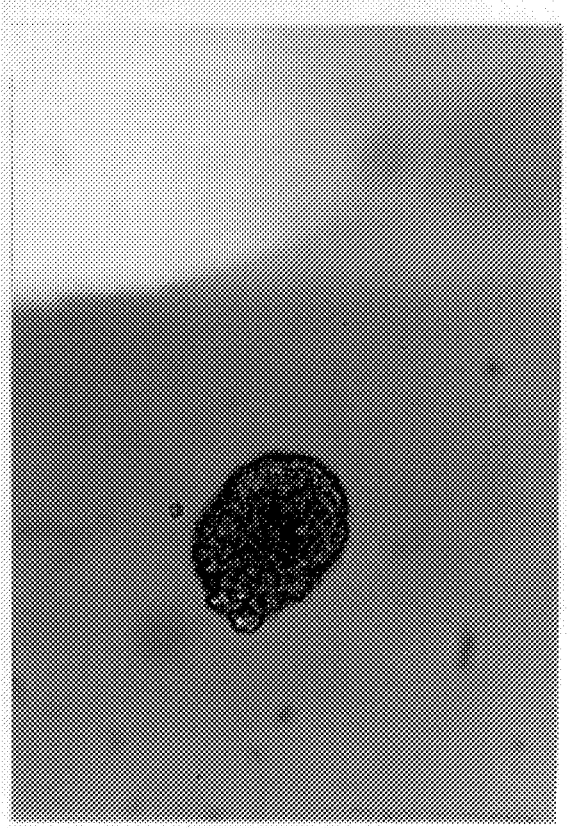
FIG. 2 shows an islet grown according to the subject invention.
Figure 1D:
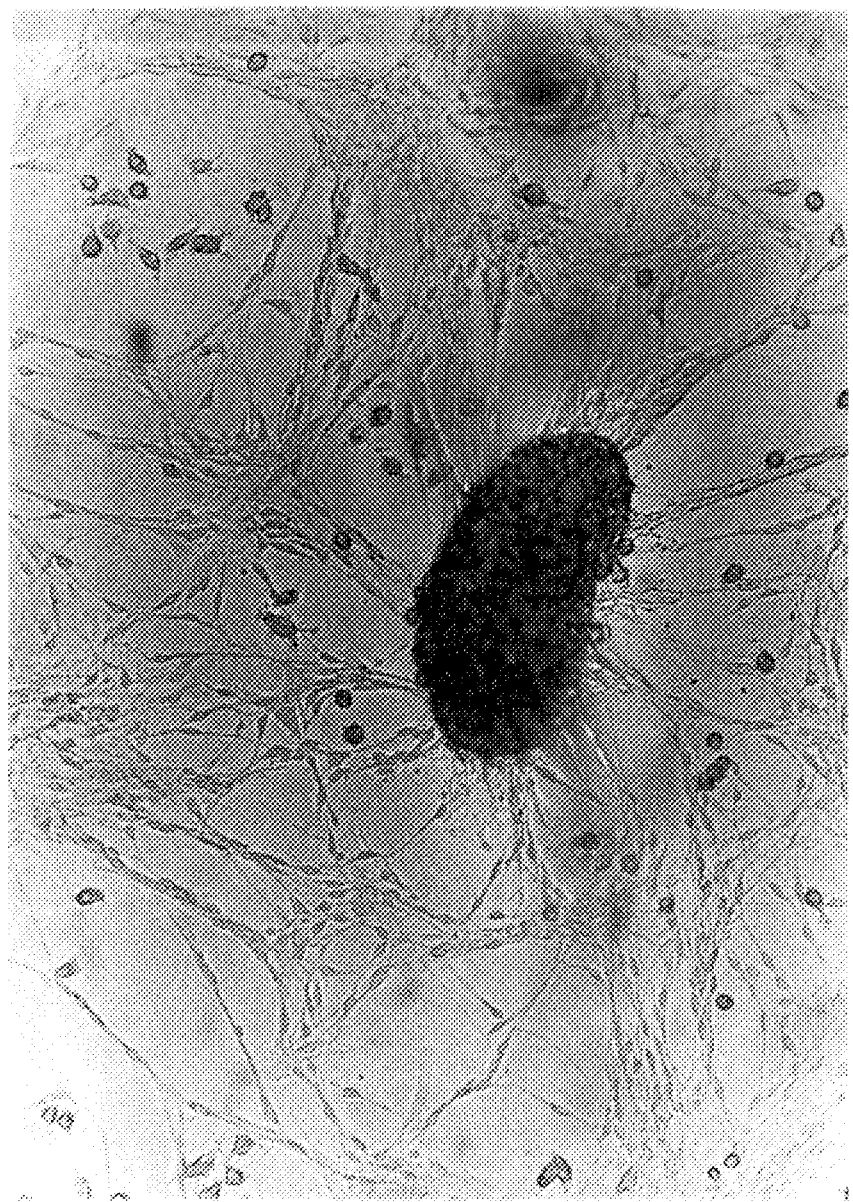

The islet-like structures, collected after natural detachment or removal from the stromal layers using a Pasteur pipette, were gently washed in medium, then broken into single cell suspensions by reflux pipetting. Single cell suspensions were prepared by cytocentrifugation, then stained for general morphology and insulin production. At least three distinct cell types are identifiable and appear similar to islet cells prepared from islets of control mice. Furthermore, the major population of cells stained positive with anti-insulin antibody, indicating the major cell type contained in the cultured islet is an insulin-producing β cell. FIGS. 1A through 1D show the various cell types which develop during the culture process. FIG. 2 shows a well-developed islet.

EXAMPLE 2

Culturing of Human Islets cells

For culturing human islet cells a procedure similar to that described in Example 1 can be utilized. The procedure of the subject invention is particularly advantageous because it is not necessary to utilize fetal cells to initiate the cell culture. In a preferred embodiment, the human cells can be suspended in Click's EHAA medium (or equivalent thereof) and supplemented with normal human serum. The cultures should be left undisturbed with no refeeding, preferably for several weeks. After about 4–5 weeks, differentiation can be initiated by refeeding the cultures with Click's EHAA medium supplemented with normal human serum. Islet cells can subsequently be collected as described in Example 1.

It should be understood that the examples and embodiments described herein are for illustrative purposes only and that various modifications or changes in light thereof will be suggested to persons skilled in the art and are to be included within the spirit and purview of this application and the scope of the appended claims.

References

Eisenbarth, G. S., (1986) *N. Engl. J. Med.* 314:1360.
Cahil, G. F., and H. O. McDevitt (1981) *N. Engl. J. Med.* 304:1454.
Todd, J. A., et al. (1989) *Nature* 338:587.
Prochazka, M., D. V. Serreze, S. M. Worthen, and E. H. Leiter (1989) *Diabetes* 38:1446.
Baekkeskov, S., et al., (1982) *Nature* 298:167.
Baekkeskov, S., et al. (1990) *Nature* 347:151.
Reddy, S., N. J. Bibby, and R. B. Elliot (1988) *Diabetologia* 31:322.
Pontesilli, O., P. Carotenuto, L. S. Gazda, P. F. Pratt, and S. J. Prowse (1987) *Clin. Exp. Immunol.* 70:84.
Wang, Y., L. Hao, R. G. Gill, and K. J. Lafferty (1987) *Diabetes* 36:535.
Karjalainen et al. (1992) *N. Engl. J. Med.* 327:302.
Serreze, D. V., E. H. Leiter, E. L. Kuff, P. Jardieu, and K. Ishizaka (1988) *Diabetes* 37:351
Signore, A, P. Pozzilli, E. A. M. Gale, D. Andreani, and P. C. L. Beverly (1989) *Biabetologia* 32:282.
Jarpe, A. J., M. Hickman, J. T. Anderson, W. E. Winter, and A. B. Peck (1991) *Regional Immunol.* 3:305
Bendelac, A., C. Carnaud, C. Boitard, and J. F. Bach (1987) *J. Exp. Med* 166:823.
Miller, B. J., M. C. Appel, J. J. O'Neil, and L. S. Wicker (1988) *J. Immunol.* 140:52.
Hanafusa T. et al. (1988) *Diabetes* 37:204.
Bendelac A. et al. (1988) *J. Immunol.* 141:2625.
Rossini, A. A., J. P. Mordes, and E. S. Handler (1988) *Diabetes* 37:257.
Nerup, J., et al. (1989) *Diabetes Care* 11:16.
Kanazawa, Y., et al. (1984) *Diabetologia* 27:113.
Anderson, J. T., J. G. Cornelius, A. J. Jarpe, W. E. Winter and A. B. Peck (1993) *Autoimmunity* 15:113.
Shieh, D. C., J. G. Cornelius, W. E. Winter, and A. B. Peck (1993) *Autoimmunity* 15:123.
Peck, A. B., and F. H. Back (1973) *J. Immunol. Methods* 3:147.

We claim:

1. A method for the production of islet cells comprising culturing mammalian pancreatic stem cells in a nutrient medium supplemented with serum from the same mammalian species, growing the stem cells for at least three weeks allowing for the establishment of mature stromal cells and initiating the differentiation of said stromal cells into islet cells by adding serum from the same mammalian species.

2. The method according to claim 1, wherein the islet cells are human islet cells and the serum is human serum.

3. The method according to claim 1, wherein the islet cells are mouse islet cells and the serum is mouse serum.

4. The method according to claim 1, wherein differentiation of cultured stem cells is initiated at about 4 to 5 weeks of culture growth by addition of serum.

5. The method according to claim 1 wherein said nutrient medium comprises a high amino acid nutrient medium.

6. The method according to claim 1 further comprising, after the step of initiating differentiation by added serum, refeeding with said serum at about one-week intervals.

7. A method for producing insulin comprising culturing mammalian pancreatic stem cells in a nutrient medium supplemented with serum from the same mammalian species, growing the stem cells for at least three weeks allowing for the establishment of mature stromal cells, initiating the differentiation of said stromal cells into islet cells by adding serum from the same mammalian species and recovering the insulin.

8. The method according to claim 7, wherein said insulin is human insulin.

9. The method according to claim 7, wherein said insulin is mouse insulin.

10. The method according to claim 7, wherein differentiation is initiated at about 4 to 5 weeks of culture growth by refeeding with medium comprising normal serum.

* * * * *